US011413266B2

(12) United States Patent
Biró et al.

(10) Patent No.: US 11,413,266 B2
(45) Date of Patent: Aug. 16, 2022

(54) USE OF CANNABINOIDS IN THE TREATMENT OF INFLAMMATORY SKIN DISEASES

(71) Applicant: GW Pharma Limited, Cambridge (GB)

(72) Inventors: Tamás Biró, Debrecen (HU); Colin Stott, Cambridge (GB); Vincenzo Di Marzo, Naples (IT)

(73) Assignee: GW Pharma Limited, Cambridge (GB)

( * ) Notice: Subject to any disclaimer, the term of this patent is extended or adjusted under 35 U.S.C. 154(b) by 0 days.

(21) Appl. No.: 15/763,186

(22) PCT Filed: Sep. 29, 2016

(86) PCT No.: PCT/GB2016/053027
§ 371 (c)(1),
(2) Date: Mar. 26, 2018

(87) PCT Pub. No.: WO2017/055846
PCT Pub. Date: Apr. 6, 2017

(65) Prior Publication Data
US 2018/0263952 A1  Sep. 20, 2018

(30) Foreign Application Priority Data
Sep. 29, 2015 (GB) .................. 1517215

(51) Int. Cl.
*A61K 31/352* (2006.01)
*A61K 31/047* (2006.01)
(Continued)

(52) U.S. Cl.
CPC .......... *A61K 31/352* (2013.01); *A61K 9/0014* (2013.01); *A61K 31/047* (2013.01); *A61K 31/191* (2013.01); *A61K 45/06* (2013.01)

(58) Field of Classification Search
CPC ..................... A61K 31/352; A61K 31/047
(Continued)

(56) References Cited

U.S. PATENT DOCUMENTS 7,807,711 B2 * 10/2010 Korthout .............. A61K 36/185
514/454
2008/0255224 A1  10/2008 Blum
(Continued)

FOREIGN PATENT DOCUMENTS

CA    2 910 206 A1   12/2015
EP    2 444 081 A1    4/2012
(Continued)

OTHER PUBLICATIONS

Sarris et al, Annals of Oncology 1999, vol. 10, pp. 433-440 (Year: 1999).*
Arican et al, Meidators of Inflammation 2005, vol. 5, oo.273-279 (Year: 2005).*
Travers et al, J Allergy Clin Immunol 2010, vol. 125, pp. 146-152 (Year: 2010).*
(Continued)

*Primary Examiner* — Craig D Ricci
*Assistant Examiner* — Janet L Coppins
(74) *Attorney, Agent, or Firm* — Wolf, Greenfield & Sacks, P.C.

(57) ABSTRACT

The present invention relates to the use of one or more cannabinoids in the treatment of an inflammatory skin disease. Preferably the one or more cannabinoids are taken from the group consisting of: cannabidiol (CBD), cannabidiolic acid (CBDA), cannabidivarin (CBDV), cannabigerol (CBG), cannabigervarin (CBGV) and tetrahydrocannabivarin (THCV). The inflammatory skin disease may be caused by one or more of the following: microbial infection-induced dermatitis; solar dermatitis; atopic dermatitis; and allergic contact dermatitis.

5 Claims, 12 Drawing Sheets

(51) Int. Cl.
  *A61K 45/06* (2006.01)
  *A61K 31/191* (2006.01)
  *A61K 9/00* (2006.01)
(58) Field of Classification Search
  USPC .......................................................... 514/451
  See application file for complete search history.

(56) References Cited

U.S. PATENT DOCUMENTS

| | | | |
|---|---|---|---|
| 2010/0273895 A1* | 10/2010 | Stinchcomb | A61K 9/0014 |
| | | | 514/733 |
| 2015/0086494 A1 | 3/2015 | Sekura et al. | |
| 2015/0126595 A1* | 5/2015 | Smith | A61K 31/353 |
| | | | 514/454 |

FOREIGN PATENT DOCUMENTS

| | | | |
|---|---|---|---|
| GB | 2 450 493 | A | 12/2008 |
| GB | 2 516 335 | A | 1/2015 |
| WO | WO 2010/013240 | A1 | 2/2010 |
| WO | WO 2013/006729 | A2 | 1/2013 |

OTHER PUBLICATIONS

Hong et al, Semin Cutan Med Surg (2013), vol. 30 (2), pp. 71-86. (Year: 2013).*
GB1517215.8, Jun. 20, 2016, Combined Search and Examination Report.
PCT/GB2016/053027, Dec. 15, 2016, International Search Report and Written Opinion.
PCT/GB2016/053027, Apr. 3, 2018, International Preliminary Report on Patentability.
Oláh et al., Cannabidiol exerts sebostatic and anti-inflammatory effects on human sebocytes. J Clin Invest. Sep. 2014;124(9):3713-24. doi: 10.1172/JCI64628. Epub Jul. 25, 2014.
Tony, CBD for Skin Conditions—Cannabidiol Salve, Balms, Creams. CBD Blog: Buy CBD Oil Online. Jun. 13, 2014. 8 pages, http://www.buycbdonline.info/2014/06/cbd-skin-conditions/.
Tubaro et al., Comparative topical anti-inflammatory activity of cannabinoids and cannabivarins. Fitoterapia. Oct. 2010;81(7):816-9. doi: 10.1016/j.fitote.2010.04.009. Epub May 5, 2010.
Wilkinson et al., Cannabinoids inhibit human keratinocyte proliferation through a non-CB1/CB2 mechanism and have a potential therapeutic value in the treatment of psoriasis. J Dermatol Sci. Feb. 2007;45(2):87-92. Epub Dec. 6, 2006.

* cited by examiner

USE OF CANNABINOIDS IN THE TREATMENT OF INFLAMMATORY SKIN DISEASES

RELATED APPLICATION

This Application is a national stage filing under 35 U.S.C. 371 of International Application No. PCT/GB2016/053027, filed Sep. 29, 2016, the content of which is incorporated by reference herein in its entirety.

FIELD OF THE INVENTION

The present invention relates to the use of one or more cannabinoids in the treatment of an inflammatory skin disease.

Preferably the one or more cannabinoids are taken from the group consisting of: cannabidiol (CBD), cannabidiolic acid (CBDA), cannabidivarin (CBDV), cannabigerol (CBG), cannabigervarin (CBGV) and tetrahydrocannabivarin (THCV).

The inflammatory skin disease may be caused by one or more of the following: microbial infection-induced dermatitis; solar dermatitis; atopic dermatitis; and allergic contact dermatitis.

Preferably the inflammatory skin disease to be treated is one or more of: acne; alopecia areata; basal cell carcinoma; Bowen's disease; congenital erythropoietic porphyria; contact dermatitis; Darier's disease; dystrophic epidermolysis bullosa; eczema (atopic eczema); epidermolysis bullosa simplex; erythropoietic protoporphyria; fungal infections of nails; Hailey-Hailey disease; herpes simplex; hidradenitis suppurativa; hirsutism; hyperhidrosis; ichthyosis; impetigo; keloids; keratosis pilaris; lichen planus; lichen sclerosus; melisma; pemphigus vulgaris; plantar warts (verrucas); pityriasis lichenoides; polymorphic light eruption; psoriasis; pyoderma gangrenosum; rosacea; scabies; shingles; squamous cell carcinoma; Sweet's syndrome; and vitiligo.

The cannabinoids may be used concomitantly with one or more other medicaments. Alternatively the cannabinoids may be formulated for administration separately, sequentially or simultaneously with one or more medicaments or the combination may be provided in a single dosage form. Where the cannabinoid is formulated for administration separately, sequentially or simultaneously it may be provided as a kit or together with instructions to administer the one or more components in the manner indicated. It may also be used as the sole medication, i.e. as a monotherapy.

Alternatively in a separate embodiment the present invention relates to one or more cannabinoids as a cosmetic treatment for skin.

Preferably the one or more cannabinoids are taken from the group consisting of: cannabidiol (CBD), cannabidiolic acid (CBDA), cannabidivarin (CBDV), cannabigerol (CBG), cannabigervarin (CBGV) and tetrahydrocannabivarin (THCV).

Such cosmetic skin treatments may include creams and sunscreens.

BACKGROUND TO THE INVENTION

Inflammatory skin diseases are one of the most common dermatological problems that occur. Such inflammatory skin diseases range from simple rashes that occur in combination with itching and redness, to chronic conditions such as dermatitis, eczema, rosacea, seborrheic dermatitis, and psoriasis.

Skin inflammation can be characterized as acute or chronic. Acute inflammation can result from exposure to UV radiation, ionizing radiation, allergens, or to contact with chemical irritants. This type of inflammation is typically resolved within 1 to 2 weeks with little accompanying tissue destruction. In contrast, chronic inflammation results from a sustained immune cell mediated inflammatory response within the skin itself. This inflammation is long lasting and can cause significant and serious tissue destruction.

The process of skin inflammation is complex and is still not completely understood. When the skin is exposed to a "triggering" stimulus, such as UV radiation, an irritant, or allergens, the cells in the skin produce a variety of inflammatory "hormones" called cytokines and chemokines. These "inflammatory messengers" bind to specific receptors on target cells and stimulate the production of additional inflammatory signalling hormones. Some of these cause vasodilation while others activate nerve cells.

Other cytokines cause immune cells to leave the blood and migrate into the skin where they then produce more inflammatory hormones, as well as enzymes, free radicals, and chemicals that damage the skin. The end result of the initial triggering event is the amplification of a large inflammatory response that, while designed to help the skin fight infection from e.g. invading bacteria, actually causes considerable damage to the skin.

The skin, in particular the keratinocytes in the skin, are a potent source of many cytokines. Certain inflammatory skin diseases are associated with overproduction of cytokines, an alteration in cytokine receptors or dysregulation of cytokines. (Sauder, 1990).

The cytokine IL-1 is known to stimulate production of the cytokines IL-6 and IL-8 once a cytokine cascade is set in motion caused by trauma, bacterial toxins or UV light. Such overproduction of cytokines then causes release of other cytokines and an inflammatory response.

Inflammatory skin diseases such as psoriasis and atopic dermatitis can be caused by the overproduction of cytokines. For example the cytokines IL-1, IL-6 and IL-8 have all been found to be over-expressed in psoriatic plaques, (Sauder, 1990). In atopic dermatitis, also known as atopic eczema, during the chronic phase, there is activation of TNF-alpha and IL-8 and IL-12 cytokines, (Nedoszytko et al., 2014).

Allergic contact dermatitis (ACD), a form of delayed type hypersensitivity, is a prototypical T-cell-mediated skin inflammatory response that occurs after cutaneous exposure to an allergen. Following primary application to the skin, epidermal Langerhans cells (LCs) take up allergen, process it and migrate towards the regional lymph nodes, where the antigen is presented to naïve T cells which, when activated, migrate towards peripheral tissues. During this process, known as "the sensitization phase", LCs convert from a "resting" into an "activated" functional state.

Secondary allergen application induces "the elicitation phase" of ACD that involves the degranulation of mast cells, vasodilatation and influx of neutrophils, followed by substantial leukocyte infiltration into tissue and oedema formation peaking between 24 and 48 hours.

This late-phase response has the same direct effects on the skin as primary allergen contact during sensitization Although many studies report anti-inflammatory properties for two major cannabinoids present in marijuana such as the psychoactive compound tetrahydrocannabinol (THC) and the non-psychoactive compound cannabidiol (CBD), the first evidence of the anti-inflammatory effects of cannabinoids in an animal model of ACD has been reported by Karsak et al. (2007).

In particular, it was demonstrated that both subcutaneous and topical application of THC attenuated ACD in 2,4-dinitrofluorobenzene (DNFB)-treated wild-type mice. THC significantly decreased ear swelling and reduced the recruitment of Gr-1 positive granulocytes in comparison to untreated mice.

Currently the most effective and commonly used prescription drugs for treating inflammation are the corticosteroids, particularly the glucocorticoid related steroids. They are very effective for many forms of eczema, including atopic dermatitis, and are fairly effective in ameliorating the symptoms of psoriasis.

Corticosteroids are not particularly effective, however, in treating acute inflammation, like UV-induced sunburn, which is not primarily an immune cell driven inflammatory response.

Corticosteroids can be used topically or orally. Topical corticosteroids have been classified into groups based on potency. For example, the corticosteroid clobetasol proprionate, is ranked as a very potent steroid, while betametasone diproprionate and fluocinolone acetonide can range from potent to moderately potent. Whilst those containing hydrocortisone are the least potent.

While current treatment regimens for most inflammatory skin diseases are dominated by topical or oral corticosteroids, these are typically used for only short periods of time because they exert some negative side effects on skin, including:

1. Anti-proliferative/thinning effect on the skin;
2. Suppression of the skin's ability to respond to infection (immunosuppression);
3. Elevation of blood glucose levels (hyperglycemia); and
4. Impairment of adrenal gland function.

It was found that a non-psychotropic cannabinoid cannabidiol (CBD), exerted anti-acne effects (Oláh et al., 2014). Neither viability or basal sebaceous lipid synthesis were altered, however CBD normalized pro-acne agents and induced seborrhoea-mimicking lipogenesis.

CA 2910206 describes a composition comprising tetrahydrocannabinol (THC) and CBD in combination with a corticosteroid for the treatment of psoriasis.

WO 2010/013240 describes the anti-inflammatory effect of CBD and suggests it may be of use in the treatment of psoriasis and atopic dermatitis.

Tubaro et al. (2010) describe the topical anti-inflammatory action of CBD and CBDV.

WO 2013/006729 describes a nano-enhanced patch containing CBD which may be used in the treatment of psoriasis.

Wilkinson et al. describes that cannabinoids are able to inhibit human keratinocyte proliferation via a non CB1/CB2 mechanism and have a potential therapeutic value in the treatment of psoriasis.

US 2015/086494 describes an anti-inflammatory cream which comprises THC and CBD in addition to hydrocortisone.

GB 2516335 describes the use of phytocannabinoids in the treatment of skin carcinomas.

It is desirable to find new compounds which demonstrate the ability to treat inflammatory skin diseases. In particular such compounds should exert less negative side effects than corticosteroids.

The present invention demonstrates in three different models of inflammatory skin disease that certain cannabinoids are able to reduce the levels of inflammatory cytokines which are produced in response to an inflammatory insult such as microbial activity, UV light or trauma.

BRIEF SUMMARY OF THE DISCLOSURE

In accordance with a first aspect of the present invention there is provided one or more of the cannabinoids selected from the group consisting of: cannabidiol (CBD), cannabidiolic acid (CBDA), cannabidivarin (CBDV), cannabigerol (CBG), cannabigervarin (CBGV) and tetrahydrocannabivarin (THCV) for use in the treatment of an inflammatory skin disease.

Preferably the inflammatory skin disease is a microbial infection-induced dermatitis; a solar dermatitis; or an atopic dermatitis.

More preferably the inflammatory skin disease is one or more of: acne; alopecia areata; basal cell carcinoma; Bowen's disease; congenital erythropoietic porphyria; contact dermatitis; Darier's disease; dystrophic epidermolysis bullosa; eczema (atopic eczema); epidermolysis bullosa simplex; erythropoietic protoporphyria; fungal infections of nails; Hailey-Hailey disease; herpes simplex; hidradenitis suppurativa; hirsutism; hyperhidrosis; ichthyosis; impetigo; keloids; keratosis pilaris; lichen planus; lichen sclerosus; melisma; pemphigus vulgaris; plantar warts (verrucas); pityriasis lichenoides; polymorphic light eruption; psoriasis; pyoderma gangrenosum; rosacea; scabies; shingles; squamous cell carcinoma; Sweet's syndrome; and vitiligo.

Most preferably the inflammatory skin disease to be treated is eczema (atopic eczema) or psoriasis.

Most preferably the cannabinoid is cannabidiol acid (CBDA) or cannabigerol (CBG).

In one embodiment the cannabinoid is in the form of a highly purified extract of cannabis such that it is present at greater than 95% of the total extract (w/w).

Alternatively the cannabinoid is synthetically produced.

Preferably the cannabinoid is used at a dose of less than 2000 mg.

More preferably the cannabinoid is used at a dose of between 10 and 1000 mg, depending on the bioavailability of the cannabinoid, thus the range may encompass any dose between such as greater or less than 50, 100, 200, 400, 600, and 800 mg.

In a further embodiment the cannabinoid is used concomitantly with one or more other medicaments. Preferably the one or more other medicaments is a corticosteroid.

In accordance with a second aspect of the present invention there is provided a method of treating an inflammatory skin disease comprising administering one or more of the cannabinoids selected from the group consisting of: cannabidiol (CBD), cannabidiolic acid (CBDA), cannabidivarin (CBDV), cannabigerol (CBG), cannabigervarin (CBGV) and tetrahydrocannabivarin (THCV) to a subject.

In accordance with a third aspect of the present invention there is provided a composition for use in the treatment of an inflammatory skin disease comprising one or more of the cannabinoids selected from the group consisting of: cannabidiol (CBD), cannabidiolic acid (CBDA), cannabidivarin (CBDV), cannabigerol (CBG), cannabigervarin (CBGV) and tetrahydrocannabivarin (THCV) and one or more pharmaceutically or cosmetically acceptable excipients.

Preferably the composition is an oral or topical composition.

Most preferably the composition is a pharmaceutical or a cosmetic.

In accordance with a fourth aspect of the present invention there is provided a cosmetic treatment of a skin condition comprising applying one or more of the cannabinoids selected from the group consisting of: cannabidiol (CBD), cannabidiolic acid (CBDA), cannabidivarin (CBDV), cannabigerol (CBG), cannabigervarin (CBGV) and tetrahydrocannabivarin (THCV) to a subject.

Preferably the one or more cannabinoids are taken from the group consisting of: cannabidiol (CBD), cannabidiolic acid (CBDA), cannabidivarin (CBDV), cannabigerol (CBG), cannabigervarin (CBGV) and tetrahydrocannabivarin (THCV).

Such cosmetic skin treatments may include creams and sunscreens.

Definitions

Definitions of some of the terms used to describe the invention are detailed below:

The cannabinoids described in the present application are listed below along with their standard abbreviations.

| Cannabinoids and their abbrevations | | |
|---|---|---|
| CBD | Cannabidiol | |
| CBDA | Cannabidiolic acid | |
| CBDV | Cannabidivarin | |
| CBG | Cannabigerol | |
| CBGV | Cannabigervarin | |
| THCV | Tetrahydrocannabivarin | |

The table above is not exhaustive and merely details the cannabinoids which are identified in the present application for reference. So far over 85 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoid extracts" are defined as cannabinoids that have been extracted from the cannabis plant and purified to the extent that other cannabinoids and non-cannabinoid components that are co-extracted with the cannabinoids have been substantially removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

BRIEF DESCRIPTION OF THE DRAWINGS

Embodiments of the invention are further described hereinafter with reference to the accompanying drawings, in which.

DETAILED DESCRIPTION

Figure 1:
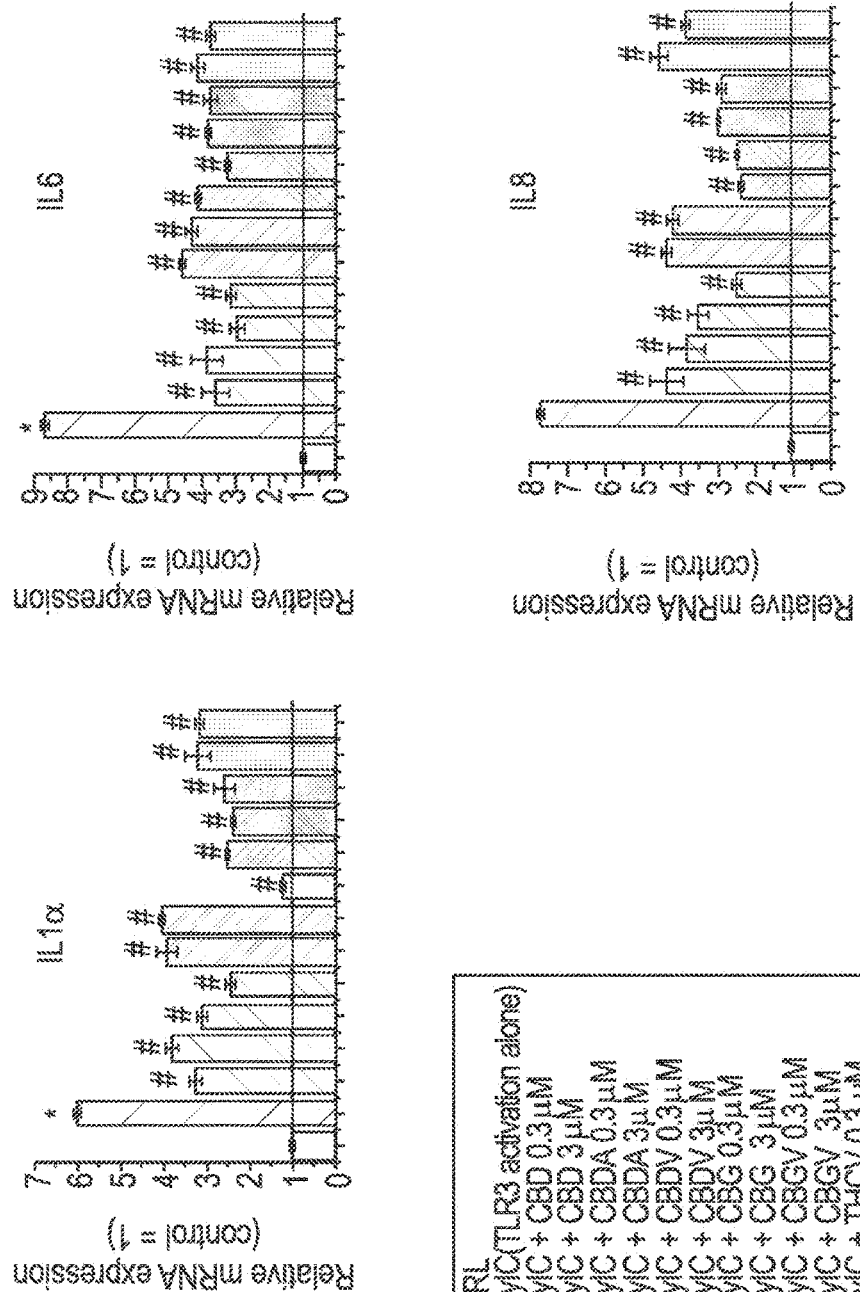
FIG. 1 shows the effects of phytocannabinoids on PolyIC-induced cytokine expression in HaCaT keratinocytes.

Example 1: Assessment of Anti-Inflammatory Effects of Phytocannabinoids (Functional In Vitro Studies)

The following example uses six different phytocannabinoids to determine the effectiveness of them in three different models of skin inflammatory diseases namely; microbial infection-induced dermatitis; solar dermatitis; and atopic dermatitis.

Different skin cell lines (HaCaT; HPV-Ker; and NHEK) were tested in the three different models to determine whether there was a significant difference between them.

There are many different forms of inflammatory skin diseases including acne; alopecia areata; basal cell carcinoma; Bowen's disease; congenital erythropoietic porphyria; contact dermatitis; Darier's disease; dystrophic epidermolysis bullosa; eczema (atopic eczema); epidermolysis bullosa simplex; erythropoietic protoporphyria; fungal infections of nails; Hailey-Hailey disease; herpes simplex; hidradenitis suppurativa; hirsutism; hyperhidrosis; ichthyosis; impetigo; keloids; keratosis pilaris; lichen planus; lichen sclerosus; melisma; pemphigus vulgaris; plantar warts (verrucas); pityriasis lichenoides; polymorphic light eruption; psoriasis; pyoderma gangrenosum; rosacea; scabies; shingles; squamous cell carcinoma; Sweet's syndrome; and vitiligo.

These diseases are all caused by inflammation of the skin and as such cannabinoids demonstrating positive results in one or more of the models of inflammatory skin diseases might suggest that such cannabinoids might be useful agents in the treatment of one or more of the inflammatory skin diseases described above.

Materials and Methods

Materials

The phytocannabinoids cannabidiol (CBD), cannabidiolic acid (CBDA), cannabidivarin (CBDV), cannabigerol (CBG), cannabigervarin (CBGV) and tetrahydrocannabivarin (THCV) were tested for their ability to decrease skin inflammation.

Following viability assays, two concentrations (0.3 and 3 μM) of each phytocannabinoid were selected which did not induce dramatic changes in cellular viability of human keratinocytes.

Lipoteichoic acid from *Staphylococcus aureus* [LTA; Toll-like receptor 2 (TLR2) activator], polyinosinic-polycytidylic acid [poly-(I:C); pIC; TLR3 activator], lipopolysaccharide (LPS; TLR4 activator) and *Staphylococcus* enterotoxin B (SEB; inflammation inductor in atopic dermatitis) were obtained from Sigma-Aldrich (St. Louis, Mo., USA).

Thymic stromal lymphopoietin (TSLP; inflammation inductor in atopic dermatitis) were purchased from eBioscience, Ltd. (Hatfield, Ireland, United Kingdom) and were diluted in water.

Cell Cultures

Human immortalized keratinocytes (HPV-Kers and HaCaTs) were cultured in serum-free EpiLife medium (Life Technologies Hungary Ltd., Budapest, Hungary) supplemented with Human Keratinocyte Growth Supplement (HKGS; in 1:100; Life Technologies Hungary Ltd.) and antibiotics (preformed mixture of penicillin and streptomycin in 1:100; PAA Laboratories GmbH, Pasching, Austria and Fungizone® Antimicotic (in 1:200; Life Technologies Hungary Ltd.) or in Dulbecco's Modified Eagle Medium (DMEM; Life Technologies Hungary Ltd.) supplemented with 10 (V/V) % fetal bovine serum (FBS; Life Technologies Hungary Ltd.) and the above mentioned antibiotics mixture with Fungizone® antimicotic, respectively.

For establishing primary normal human epidermal keratinocyte cultures (NHEKs), human skin samples were obtained after obtaining written informed consent from healthy individuals undergoing dermatosurgery, adhering to Helsinki guidelines, and after obtaining Institutional Research Ethics Committee's permission.

NHEKs were isolated after overnight dermo-epidermal separation in 2.4 IU/ml dispase (Roche Diagnostics, Berlin, Germany) by short trypsin (0.05%, Sigma-Aldrich) digestion. Cells were cultured in the same medium than the immortalized keratinocytes: EpiLife serum-free medium supplemented with Human Keratinocyte Growth Supplement, mixture of antibiotics and Fungizone® antimicotic. All cells were cultured at 37° C. in humidified, 5% CO2 containing atmosphere, the medium was changed every other day, and cells were sub-cultured at 70-80% confluence.

Determination of Cytokine Release (ELISA)

Cells were treated as indicated for 6, 24 or 48 hours. Supernatants were collected, and the released amount of interleukin IL-6 and IL-8 were determined using OptEIA kits (BD Pharmingen, Franklin Lakes, N.J., USA) and IL-1a (from the R&D Systems, Inc., Minneapolis, United States) according to the manufacturer's protocol.

UVB Irradiation

Culture medium of the cells cultivated in Petri-dishes (d=35 mm) was replaced by 800 μl colourless Sebomed Basal Medium. Lids were removed and cells were then irradiated by using a narrow-band UV-irradiation instrument (Bio-Sun microprocessor-controlled UV irradiation system; Wilber Lourmat, Marne-la-Vallee, France), with a total dose of 40 mJ/cm2 of UVB (312 nm).

Immediately after the irradiation, the medium was replaced with the conventional culture medium of the cells (see above) with or without test compounds or vehicle. Following a 6-hr culture period, cells were harvested for RT-qPCR (supernatants were also collected in all cases).

Quantitative Real-Time Polymerase Chain Reaction (RT-qPCR)

RT-qPCR experiments were performed as described previously (Oláh et al., 2014) on a Roche Light Cycler 480 QPCR System (Roche Applied Sciences) using the 5' nuclease assay. Total RNA was isolated using TRIzol (LifeTechnologies), DNase treatment was performed according to the manufacturer's protocol, and then 1 μg of total RNA were reverse-transcribed into cDNA by using High Capacity cDNA Kit from Life Technologies Corporation.

PCR amplification was performed by using the TaqMan primers and probes (assay IDs: Hs00174092_m1 for IL-1α, Hs00174097_m1 for IL-1β, Hs00985639_m1 for IL-6, Hs00174103_m1 for IL-8 and Hs00174128_m1 for tumor necrosis factor-α [TNFα]).

As internal control, expression of peptidyl-prolyl isomerase A (PPIA), glyceraldehyde-3-phosphate dehydrogenase (GAPDH) and actin beta (ACTB) was determined (assay IDs: Hs99999904_m1 for PPIA, Hs99999905_m1 for GAPDH and Hs99999903_m1 for ACTB).

The amount of the transcripts was normalized to those of the housekeeping gene using the ΔCT method. When indicated, the results were then normalized to the expression of the vehicle control or the LTA-treated culture (ΔΔCT method), and were plotted as mean±SD of 3 technical replicates.

Statistical Analysis

Data were analysed and graphs were plotted by using Origin Pro Plus 6.0 software (Microcal, Northampton, Mass., USA), using Student's two-tailed two samples t-test and $P<0.05$ values were regarded as significant differences.

Results

Determination of Effects of Phytocannabinoids on Inflammatory Response of Human Epidermal Keratinocytes Selection of Appropriate Models of Skin Inflammatory Diseases Three different cellular inflammatory models were tested in order to determine the effects of the phytocannabinoids in models of skin inflammatory diseases. These models were:

Inflammation induced by TLR3 activation. This model mimics microbial infection-induced dermatitis. In this model all 3 keratinocyte cell types were tested to determine the phytocannabinoids effects on the cytokines: IL6 and IL8 on all 3 cell types; and IL1α on HaCaT keratinocytes.

Inflammation induced by UVB irradiation. This model mimics solar dermatitis. In this model all 3 keratinocyte cell types were tested to determine the phytocannabinoids effects on the cytokines: IL6 and IL8 on all 3 cell types.

Inflammation induced by the combination of *Staphylococcus aureus* enterotoxin B (SEB) and thymic stromal lymphopoietin (TSLP). This model mimics atopic dermatitis. In this model HPV-Ker cells were tested to determine the phytocannabinoids effects on the cytokine: IL8.

A. Model of Microbial Infection-Induced Dermatitis

HaCaT Keratinocytes

In HaCaT keratinocytes, all of the phytocannabinoids (at both concentrations) resulted in a marked suppression of the TLR3-activation (by the administration of PolyIC, known ligand of TLR3) induced up-regulation of mRNA expressions of the pro-inflammatory cytokines IL1α, IL6 and IL8 (FIG. 1).

Figure 2:
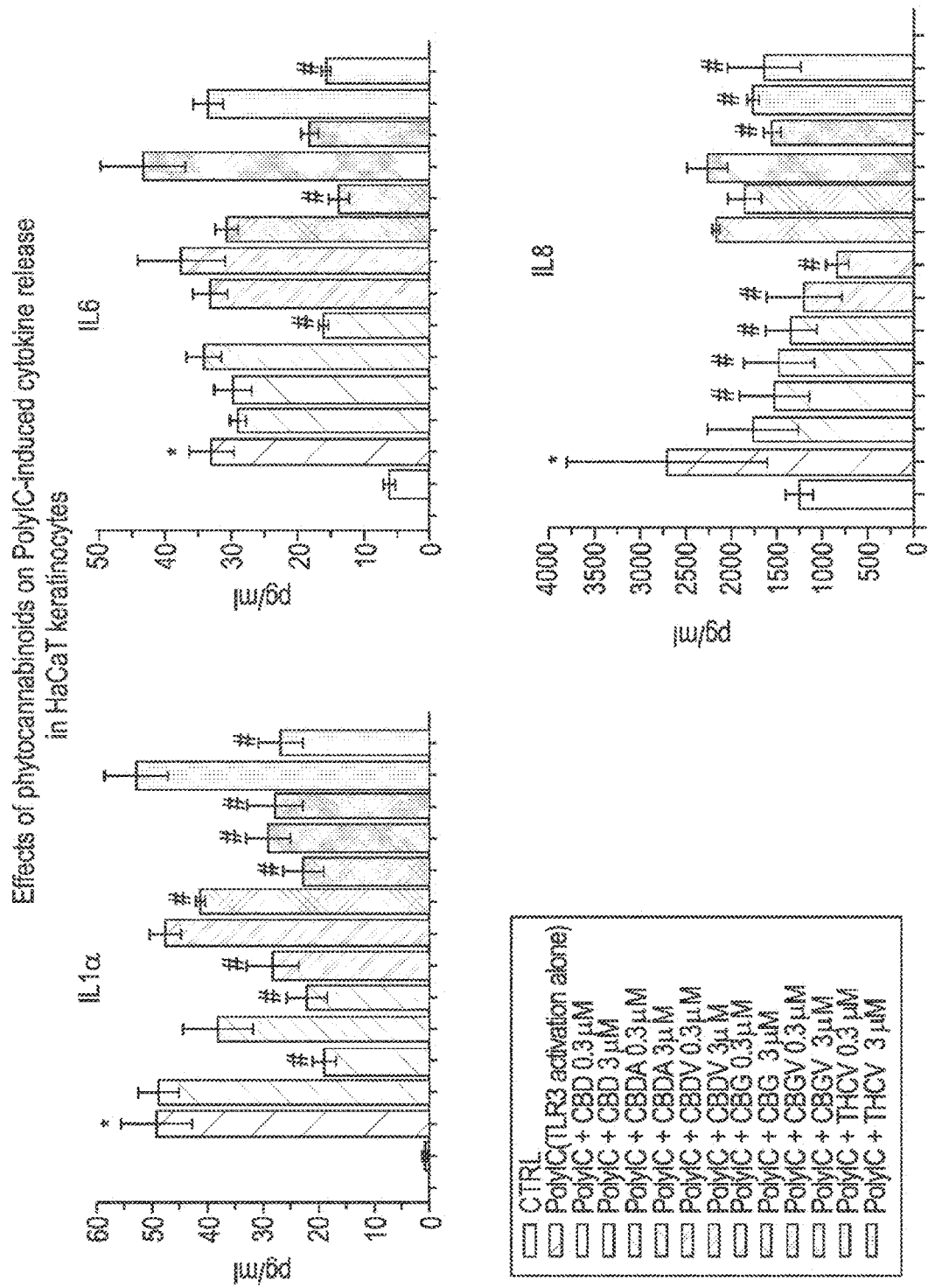
FIG. 2 shows the effects of phytocannabinoids on PolyIC-induced cytokine release in HaCaT keratinocytes.

These anti-inflammatory effects were also detected when the release of the above cytokines were tested (FIG. 2); namely, most phytocannabinoids were able to prevent the PolyIC-induced augmented secretion of the pro-inflammatory IL1α, IL6 and IL8.

HPV-Ker Keratinocytes

Figure 3:
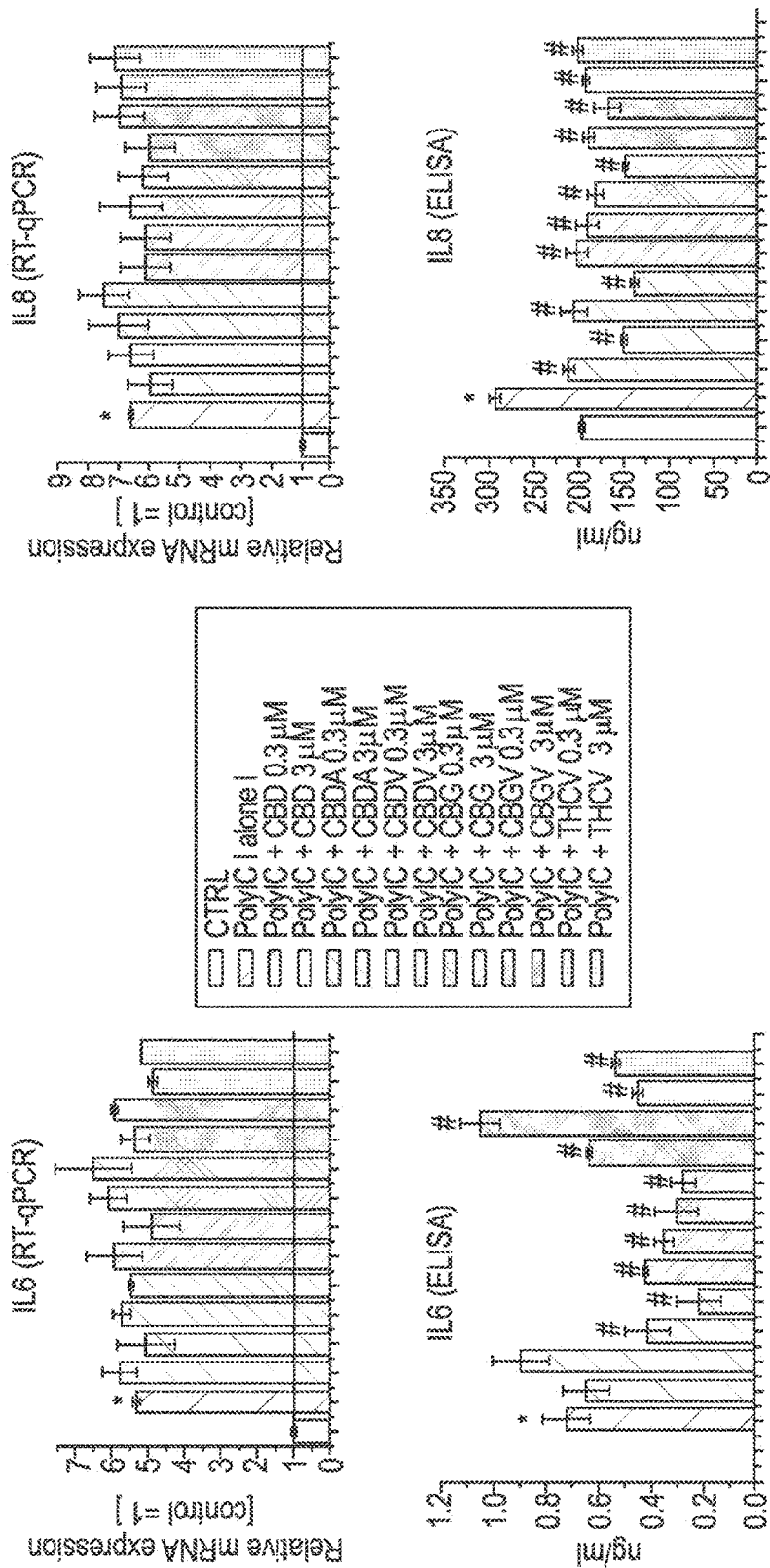
FIG. 3 shows the effects of phytocannabinoids on PolyIC-induced cytokine expression and release in HPV-Ker keratinocytes.

In HPV-KER cells, the tested phytocannabinoids did not exert any significant effect on the TLR3-activation induced up-regulation of mRNA expressions of the pro-inflammatory cytokines IL6 and IL8 (FIG. 3, upper panels).

However, as a marked contrast, all measured phytocannabinoids prevented the PolyIC-induced augmented secretion of the pro-inflammatory IL8 whereas most phytocannabinoids also exerted anti-inflammatory action on the IL6 release (FIG. 3, lower panels). In the latter case, the only exception was CBGV which, at 0.3 μM, did not affect IL6 levels whilst, at higher concentration (3 μM), significantly further augmented the TLR3-activation induced augmented release of IL6.

NHEKs

Similar to as found on HPV-Ker cells, the tested phytocannabinoids did not exert any significant effect on the TLR3-activation induced up-regulation of mRNA expressions of the pro-inflammatory cytokines IL6 and IL8 (data not shown).

Figure 4:
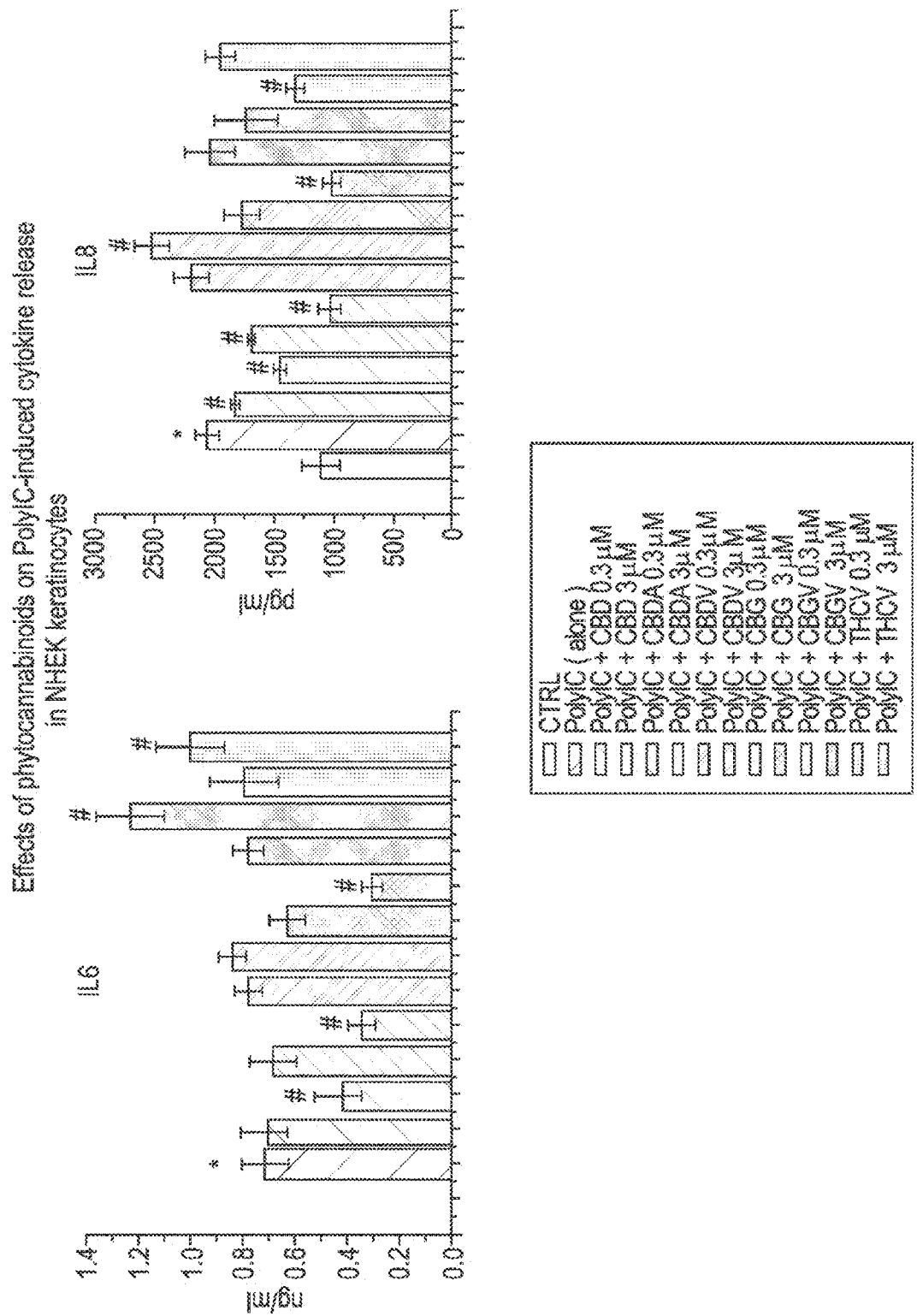
FIG. 4 shows the effects of phytocannabinoids on PolyIC-induced cytokine release in NHEK keratinocytes.

However, the phytocannabinoids induced a very heterogeneous response on the PolyIC-induced augmented secretion of the pro-inflammatory cytokines IL6 and IL8 (FIG. 4). Namely:

1. Administration of CBD, CBDA, and CBG resulted in a dose-dependent suppression of the elevated release of both IL6 and IL8.
2. CBDV did not affect the release of IL6; however, at the higher concentration, it significantly further augmented the TLR3-activation induced augmented release of IL8.
3. CBGV did not affect the release of IL8; however, at the higher concentration, it significantly further augmented the TLR3-activation induced augmented release of IL6.
4. THCV, at low concentration, did not affect the IL6 level but it significantly suppressed the elevated release of IL8.

However, at high concentration, it did not affect the release of IL8 but significantly further augmented the TLR3-activation induced augmented release of IL6.

B. Model of Solar Induced Dermatitis

HaCaT Keratinocytes

Figure 5:
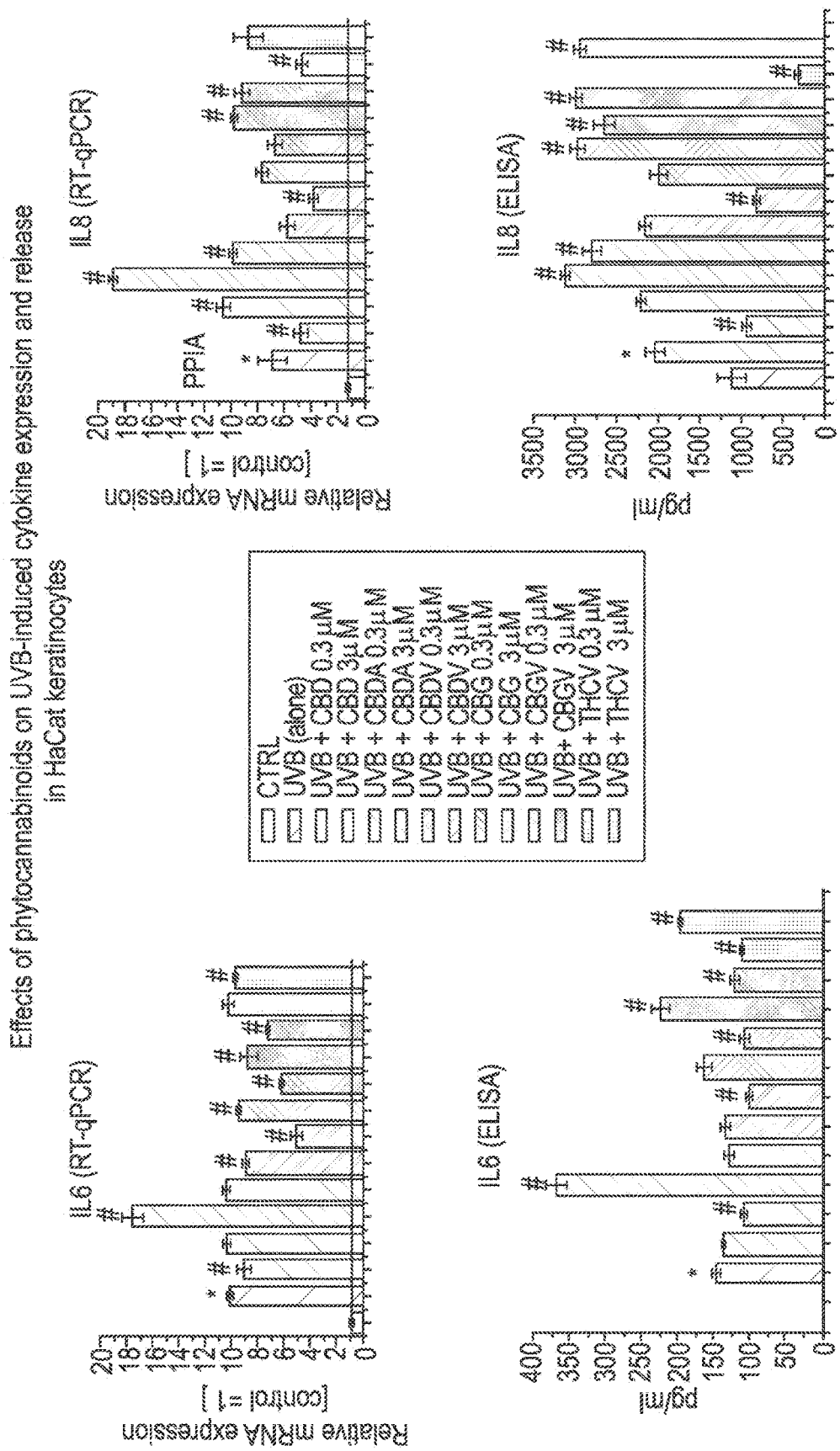
FIG. 5 shows the effects of phytocannabinoids on UVB-induced cytokine expression and release in HaCaT keratinocytes.

In HaCaT keratinocytes, the tested phytocannabinoids behaved in different ways on the mRNA and peptide levels of UVB-upregulated expressions of IL6 and IL8, depending on the concentration as described below and in FIG. 5.

CBD:
1. anti-inflammatory effects: 0.3 µM vs. IL6 and IL8 (RT-qPCR) and vs. IL8 (ELISA); 3 µM vs. IL6 (ELISA)
2. pro-inflammatory effects: 3 µM vs. IL8 (RT-qPCR)

CBDA:
1. pro-inflammatory effects: 0.3 µM vs. IL6 and IL8 (both RT-qPCR and ELISA); 3 µM vs. IL8 (both RT-qPCR and ELISA)

CBDV
1. anti-inflammatory effects: 0.3 µM vs. IL6 (RT-qPCR); 3 µM vs. IL6 and IL8 (both RT-qPCR and ELISA)

CBG
1. anti-inflammatory effects: 0.3 µM vs. IL6 (RT-qPCR); 3 µM vs. IL6 (both RT-qPCR and ELISA)
2. pro-inflammatory effects: 3 µM vs. IL8 (ELISA)

CBGV
1. anti-inflammatory effects: 0.3 µM vs. IL6 (RT-qPCR); 3 µM vs. IL6 (both RT-qPCR and ELISA)
2. pro-inflammatory effects: 0.3 µM vs. IL6 (ELISA) and IL8 (both RT-qPCR and ELISA); 3 µM vs. IL8 (both RT-qPCR and ELISA)

THCV
1. anti-inflammatory effects: 0.3 µM vs. IL6 (ELISA) and IL8 (both RT-qPCR and ELISA); 3 µM vs. IL6 (RT-qPCR)
2. pro-inflammatory effects: 3 µM vs. IL6 and IL8 (ELISA)

HPV-Ker Keratinocytes

Figure 6:
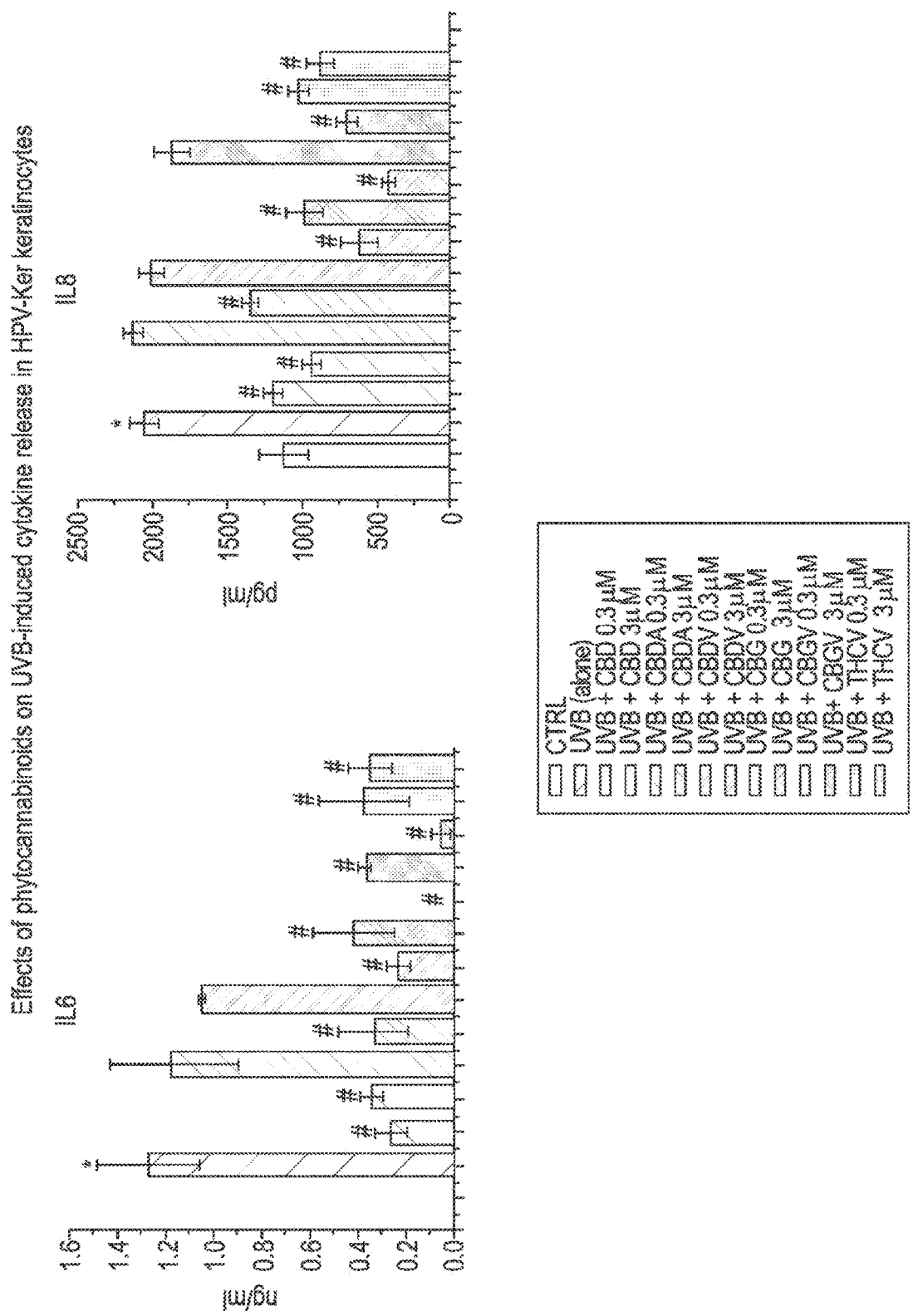
FIG. 6 shows the effects of phytocannabinoids on UVB-induced cytokine release in HPV-Ker keratinocytes.

All of the tested phytocannabinoids significantly and markedly suppressed the UVB-upregulated secretion of IL6 and IL8 (FIG. 6).

Of further importance, none of the phytocannabinoids exerted pro-inflammatory actions.

NHEKs

Figure 7:
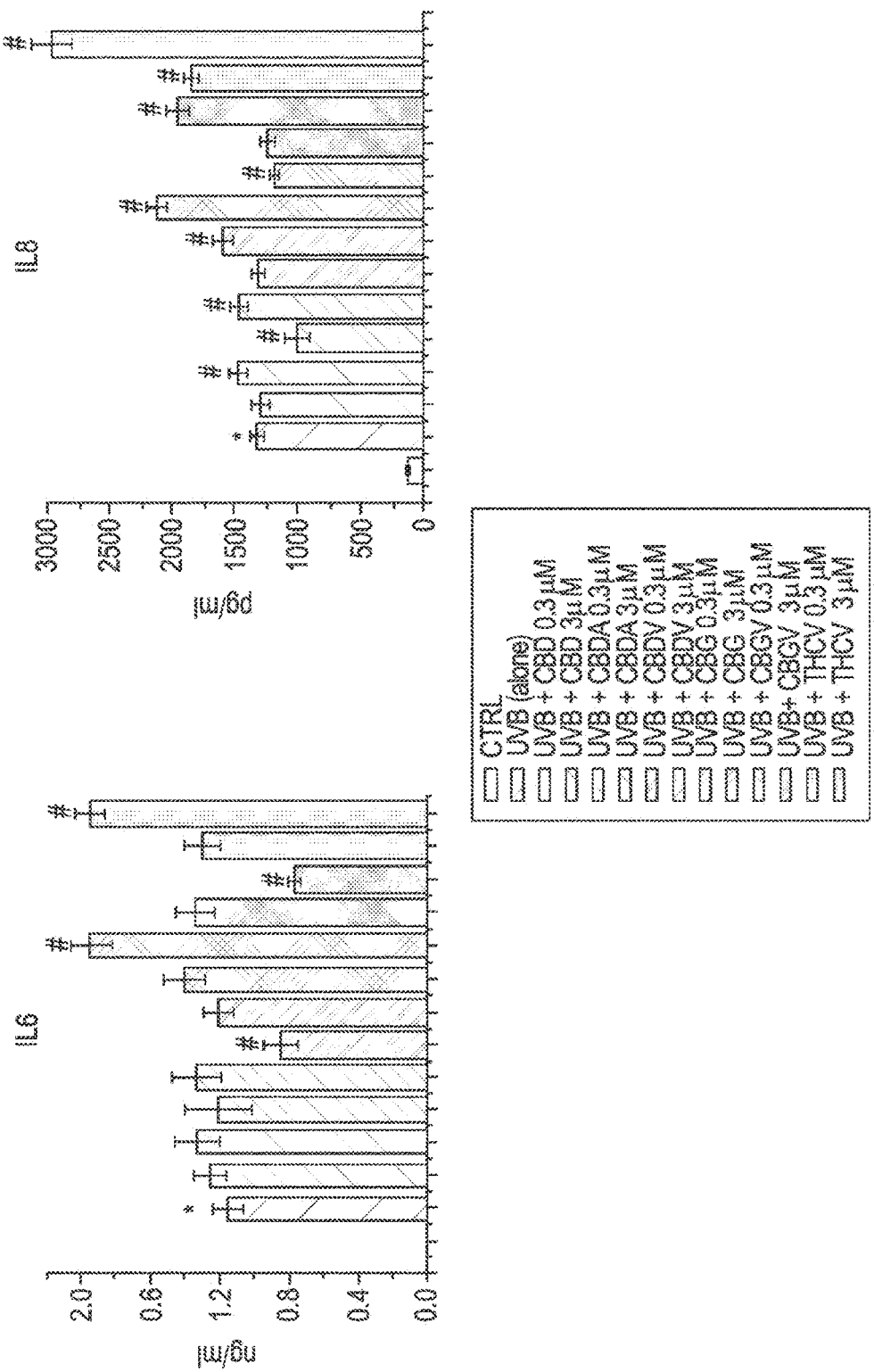
FIG. 7 shows the effects of phytocannabinoids on UVB-induced cytokine release in NHEK keratinocytes.

In NHEKs, only certain phytocannabinoids (CBGV and CBDV vs. IL6; CBDA and CBG vs. IL8), and only at given (mostly lower) concentrations, could significantly suppress the UVB-upregulated expressions of the cytokines (FIG. 7).

At higher concentrations, the phytocannabinoids (CBG and THCV vs. IL6; all vs. IL8) exhibited pro-inflammatory effects.

C. Model of Atopic Dermatitis

Figure 8:
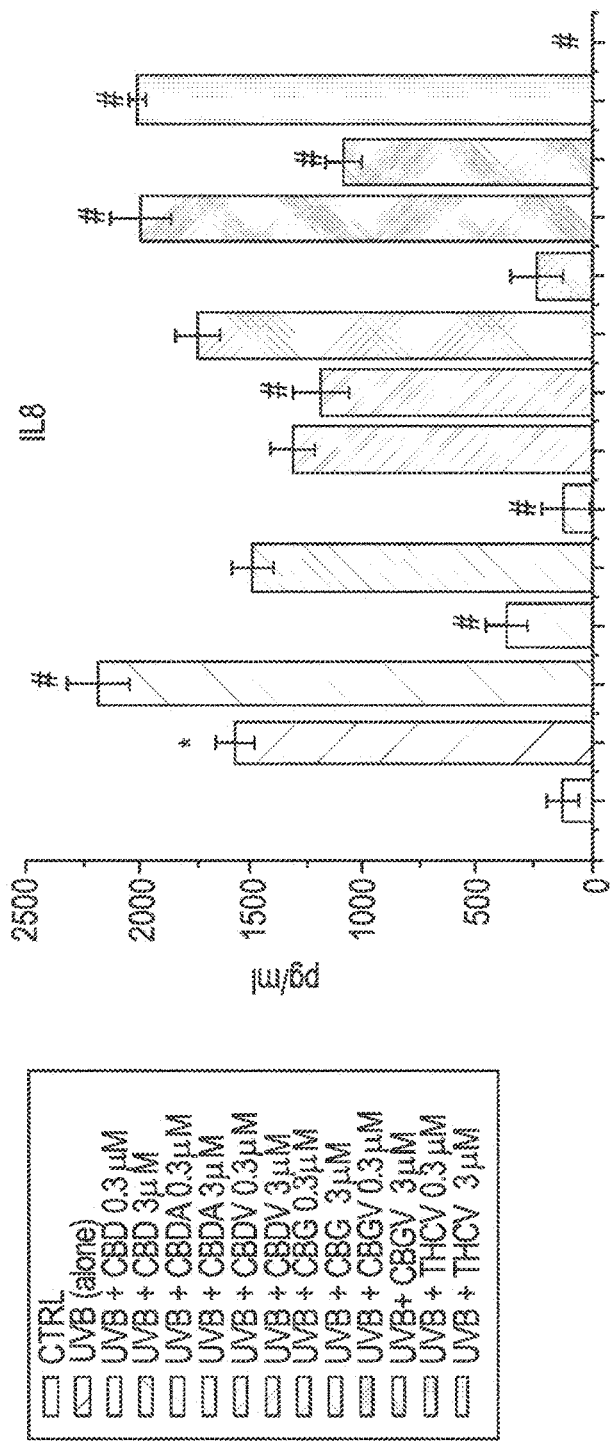
FIG. 8 shows the effects of phytocannabinoids on SEB/TSLP-induced cytokine release in HPV-Ker keratinocytes.

In this model, employed on HPV-Ker keratinocytes, higher concentrations of all tested phytocannabinoids exerted significant anti-inflammatory effects as they suppressed the SEB/TSLP-induced up-regulation of IL8 release (FIG. 8).

Of importance, lower concentrations of the phytocannabinoids either did not induce any significant effect (CBDA, CBDV, CBG) or exert pro-inflammatory actions.

Conclusions

Tables 1 to 3 below summarize the results obtained with the tested phytocannabinoids in the various keratinocyte inflammatory models.

The scores for the cannabinoids at the two concentrations are based on a score of 1 point attributed to an anti-inflammatory effect; a score of 0 points being attributed to no effect; and a score of −1 being attributed to a pro-inflammatory effect.

Table 1 demonstrates that in the TLR3-induced inflammation model, which mimics microbial infection-induced dermatitis, all phytocannabinoids exerted remarkable anti-inflammatory actions.

In particular the overall scores suggest that the cannabinoids CBDA and CBG might be most effective at the reduction of inflammation in microbial infection-induced dermatitis.

Table 2 demonstrates in the UVB-induced inflammation model, which mimics solar dermatitis, all phytocannabinoids exerted remarkable anti-inflammatory actions only on HPV-Ker keratinocytes.

Importantly, several phytocannabinoids induced pro-inflammatory actions (or did not cause measurable effects) in the other two models.

The overall scores for the cannabinoids suggest that the compounds CBDA and CBG might be most effective in the reduction of inflammation caused by UV light.

Table 3 demonstrates that in the SEB/TSLP-induced inflammation model, which mimics atopic dermatitis, all phytocannabinoids exerted remarkable, dose-dependent anti-inflammatory actions.

At lower concentrations, certain phytocannabinoids induced augmentation of inflammation suggesting that not all cannabinoids at all concentrations are suitable candidates for use in the treatment of skin inflammatory diseases. The cannabinoids that were most effective were CBDA, CBDV and CBG in the reduction of inflammation caused by SEB/TSLP.

TABLE 1

Summary of effects of phytocannabinoids on microbial infection-induced dermatitis

| Cell type | Cyto-kine | M&M | CBD 0.3 | CBD 3 | CBDA 0.3 | CBDA 3 | CBDV 0.3 | CBDV 3 | CBG 0.3 | CBG 3 | CBGV 0.3 | CBGV 3 | THCV 0.3 | THCV 3 |
|---|---|---|---|---|---|---|---|---|---|---|---|---|---|---|
| HaCaT | Il1α | qPCR | ✓ | ✓ | ✓ | ✓ | ✓ | ✓ | ✓ | ✓ | ✓ | ✓ | ✓ | ✓ |
| | | ELISA | — | ✓ | — | ✓ | ✓ | — | — | ✓ | ✓ | ✓ | — | ✓ |
| | IL6 | qPCR | ✓ | ✓ | ✓ | ✓ | ✓ | ✓ | ✓ | ✓ | ✓ | ✓ | ✓ | ✓ |
| | | ELISA | — | — | — | ✓ | — | — | — | ✓ | — | ✓ | — | ✓ |
| | IL8 | qPCR | ✓ | ✓ | ✓ | ✓ | ✓ | ✓ | ✓ | ✓ | ✓ | ✓ | ✓ | ✓ |
| | | ELISA | — | ✓ | ✓ | ✓ | ✓ | ✓ | — | — | — | ✓ | ✓ | ✓ |
| HPV-Ker | IL6 | ELISA | — | — | ✓ | ✓ | ✓ | ✓ | ✓ | ✓ | — | x | ✓ | ✓ |
| | IL8 | ELISA | ✓ | ✓ | ✓ | ✓ | ✓ | ✓ | ✓ | ✓ | ✓ | ✓ | ✓ | ✓ |

TABLE 1-continued

Summary of effects of phytocannabinoids on microbial infection-induced dermatitis

| Cell type | Cyto-kine | M&M | CBD | | CBDA | | CBDV | | CBG | | CBGV | | THCV | |
|---|---|---|---|---|---|---|---|---|---|---|---|---|---|---|
| | | | 0.3 | 3 | 0.3 | 3 | 0.3 | 3 | 0.3 | 3 | 0.3 | 3 | 0.3 | 3 |
| NHEK | IL6 | ELISA | — | ✓ | — | ✓ | — | — | — | ✓ | — | x | — | x |
| | IL8 | ELISA | ✓ | ✓ | ✓ | ✓ | — | x | — | ✓ | — | — | ✓ | — |
| | SCORE | | 5 | 8 | 7 | 10 | 7 | 5 | 5 | 9 | 5 | 5 | 7 | 7 |

Key:
✓ anti-inflammatory effect
— no effect
x pro-inflammatory effect

TABLE 2

Summary of effects of phytocannabinoids on solar induced dermatitis

| Cell type | Cyto-kine | M&M | CBD | | CBDA | | CBDV | | CBG | | CBGV | | THCV | |
|---|---|---|---|---|---|---|---|---|---|---|---|---|---|---|
| | | | 0.3 | 3 | 0.3 | 3 | 0.3 | 3 | 0.3 | 3 | 0.3 | 3 | 0.3 | 3 |
| HaCaT | IL6 | qPCR | ✓ | — | x | — | ✓ | ✓ | ✓ | ✓ | ✓ | ✓ | — | ✓ |
| | | ELISA | — | ✓ | x | — | — | ✓ | — | ✓ | x | ✓ | ✓ | x |
| | IL8 | qPCR | ✓ | x | x | x | — | ✓ | — | — | x | x | ✓ | — |
| | | ELISA | ✓ | — | x | x | — | ✓ | — | x | x | x | ✓ | x |
| HPV-Ker | IL6 | ELISA | ✓ | ✓ | — | ✓ | — | ✓ | ✓ | ✓ | ✓ | ✓ | ✓ | ✓ |
| | IL8 | ELISA | ✓ | ✓ | — | ✓ | — | ✓ | ✓ | — | ✓ | ✓ | ✓ | ✓ |
| NHEK | IL6 | ELISA | — | — | — | — | ✓ | — | — | — | x | — | ✓ | x |
| | IL8 | ELISA | — | x | ✓ | x | — | x | x | ✓ | — | x | x | x |
| | SCORE | | 5 | 1 | 1 | -1 | 2 | 5 | 2 | 3 | -1 | 2 | 4 | 0 |

Key:
✓ anti-inflammatory effect
— no effect
x pro-inflammatory effect

TABLE 3

Summary of effects of phytocannabinoids on atopic dermatitis

| Cell type | Cyto-kine | M&M | CBD | | CBDA | | CBDV | | CBG | | CBGV | | THCV | |
|---|---|---|---|---|---|---|---|---|---|---|---|---|---|---|
| | | | 0.3 | 3 | 0.3 | 3 | 0.3 | 3 | 0.3 | 3 | 0.3 | 3 | 0.3 | 3 |
| HPV-Ker | IL8 | ELISA | x | ✓ | — | ✓ | — | ✓ | — | ✓ | x | ✓ | x | ✓ |
| | SCORE | | -1 | 1 | 0 | 1 | 0 | 1 | 0 | 1 | -1 | 1 | -1 | 1 |

Key:
✓ anti-inflammatory effect
— no effect
x pro-inflammatory effect

Example 2: Assessment of Cannabidiol in a Model of Allergic Contact Dermatitis (ACD)

Methods
Cell Culture

The immortalized HaCaT cell line was cultured in DMEM supplemented with glutamine (2 mM), penicillin (400 U·ml-1), streptomycin (50 mg·ml-1) and 10% FBS at 37° C. in humidified 5% CO2.

Poly-(I:C)-Induced Allergic Contact Dermatitis (ACD) in HaCaT Cells

HaCaT cells were plated into twenty-four-well culture plates at a cell density of 2×105 cells per well, and after 1 day were stimulated with poly-(I:C) (100 μg·ml-1) or vehicle (water) and incubated for 6 h at 37° C. in 5% CO2.

To study the effect of CBD, poly-(I:C)-stimulated HaCaT cells were treated with CBD (1, -5, -10- and 20 μM) or vehicle (methanol) for the indicated times.

The effects of the other phytocannabinoids such as cannabidiol acid (CBDA), cannabidivarin (CBDV), cannabidivarinic acid (CBDVA), cannabichromene (CBC), cannabigerol (CBG), cannabigerolic acid (CBGA), cannabigevarin (CBGV), tetrahydrocannabivarin (THCV) and tetrahydrocannabivarinic acid (THCVA) (all tested at 5, -10- and 20 μM) on MCP-2 production in poly-(I:C)-stimulated HaCaT cells were also investigated.

After 6 h the supernatants were used for MCP-2 ELISA assay according to the manufacturer's instructions. Results are expressed as relative fold of pg ml-1 normalized for poly(I:C)-stimulated HaCaT cell values considered as 100% of released MCP-2.

Cell Viability

Cell viability was measured after 6 h in HaCaT cells treated with CBD (20 µM) or vehicle by using the 3-(4,5-dimethylthiazol-2yl)-2,5-diphenyl tetrazolium bromide (MTT) colorimetric assay.

Briefly, after 6 h HaCaT cells were incubated with MTT (5 mg·ml-1) for 3 h at 37° C. in 5% CO2. After 3 h HaCaT cells were lysed with DMSO and incubated for 6 h at 37° C. in 5% CO2.

Absorbance was measured at 630 nm. Results are expressed as % of cell viability, where optical density values from vehicle-treated cells were defined as 100% of cell viability.

Analysis of Endocannabinoids and Related N-Acylethanolamines

HaCaT cells were plated into six-well culture plates at a cell density of $9 \times 10^5$ cells per well, and after 1 day were stimulated with poly-(I:C) (100 µg·ml-1) and treated with CBD (20 µM) or vehicle, and incubated for 6 h at 37° C. in 5% CO2.

After 6 h the resulting cells and supernatants were subjected to measurement of endocannabinoids such as N-arachidonoyl-ethanolamine (anandamide, AEA) and 2-arachidonoyl-glycerol (2-AG), and related N-acylethanolamines such as PEA and N oleoylethanolamine (OEA).

Cells and supernatants were homogenized in a solution of chloroform/methanol/Tris-HCl 50 mM pH 7.4 (2:1:1 by vol.) containing 10 pmol of [2H]8-AEA, and 5 pmol of [2H]5-2-AG, [2H]4-PEA and [2H]2-OEA as internal deuterated standards. The lipid-containing organic phase was pre-purified by open-bed chromatography on silica gel, and fractions obtained by eluting the column with a solution of chloroform/methanol (90:10 by vol.) were analyzed by liquid chromatography-atmospheric pressure chemical ionization-mass spectrometry (LC-APCI-MS) by using a Shimadzu HPLC apparatus (LC-10ADVP) coupled to a Shimadzu (LCMS-2020) quadrupole MS via a Shimadzu APCI interface.

LC-APCI-MS analyses of AEA, 2-AG, PEA and OEA were carried out in the selected ion monitoring (SIM) mode using m/z values of molecular ions+1 for deuterated and undeuterated compounds, respectively as follows: 356 and 348 (AEA), 384.35 and 379.35 (2-AG), 304 and 300 (PEA), 328 and 326 (OEA). AEA, 2-AG, PEA and OEA levels were calculated on the basis of their area ratio with the internal deuterated standard signal areas, and their amounts (pmol) were normalized per ml of volume.

DNFB-Induced Allergic Contact Dermatitis (ACD) in Mice

A total of 10 animals per group were used in the experiments described here.

Briefly, DNFB was diluted in acetone/olive oil (4:1 by vol.) immediately before use and eight-ten week-old female C57BL/6J mice were sensitized by painting 50 µl of 0.2% DNFB on the shaved abdomen on two consecutive days. Then, mice were challenged by painting 10 µl of 0.3% DNFB on both sides of one ear on day 5.

Ear swelling was measured 24, 48 and 72 h after this first challenge by measuring the difference in ear thickness between the unchallenged and the challenged ear using an engineer's micrometer. CBD (2.5, -5- and 10 mg·kg-1) was administered intraperitoneally (i.p.) on day 5 (the day of the first challenge with DNFB), 6 and, 7 after the initial sensitization with DNFB. CBD was dissolved in DMSO and Tween-20 1%.

Data Analysis

For the determination of MCP-2, endocannabinoids, PEA and OEA, group means were compared using the one-way ANOVA followed by Newman-Keuls multiple comparison test or the Student's t-test. For the determination of cell viability, group means were compared using the Student's t-test. All determinations were performed at least in triplicate. For the determination of ear thickness, group means were compared using the one-way ANOVA followed by Tukey-Kramer multiple comparison test (n=10).

Materials

HaCaT cell line was purchased from CLS Cell Lines Service. Cell culture media, antibiotics, MTT and DNFB were purchased from Sigma-Aldrich. Poly-(I:C) was purchased from InvivoGen.

CBD, CBDA, CBDV, CBDVA, CBC, CBG, CBGA, CBGV, THCV and THCVA (>99.9% purity) were used.

AM251, AM630 and I-RTX were purchased from Tocris Bioscience. MCP-2 ELISA kit was purchased from RayBiotech, Inc. Deuterated standards-[2H]8-AEA, [2H]5-2-AG, [2H]4-PEA and [2H]2-OEA-were purchased from Cayman Chemical.

Eight to 10-week-old female C57BL/6J mice were purchased from Harlan Sprague Dawley Inc.

Results

MCP-2 Protein Levels in Poly-(I:C)-Stimulated HaCaT Cells

The effects of CBD, CBDA, CBDV, CBDVA, CBC, CBG, CBGA, CBGV, THCV and THCVA on MCP-2 protein levels in poly-(I:C)-stimulated HaCaT cells were investigated.

HaCaT cells stimulated for 6 h with poly-(I:C) (100 µg·ml-1) and treated with the vehicle of the phytocannabinoids produced significantly higher levels of the MCP-2 chemokine (FIGS. 9 and 10) as compared to vehicle-stimulated HaCaT cells (data not shown).

Figure 9:
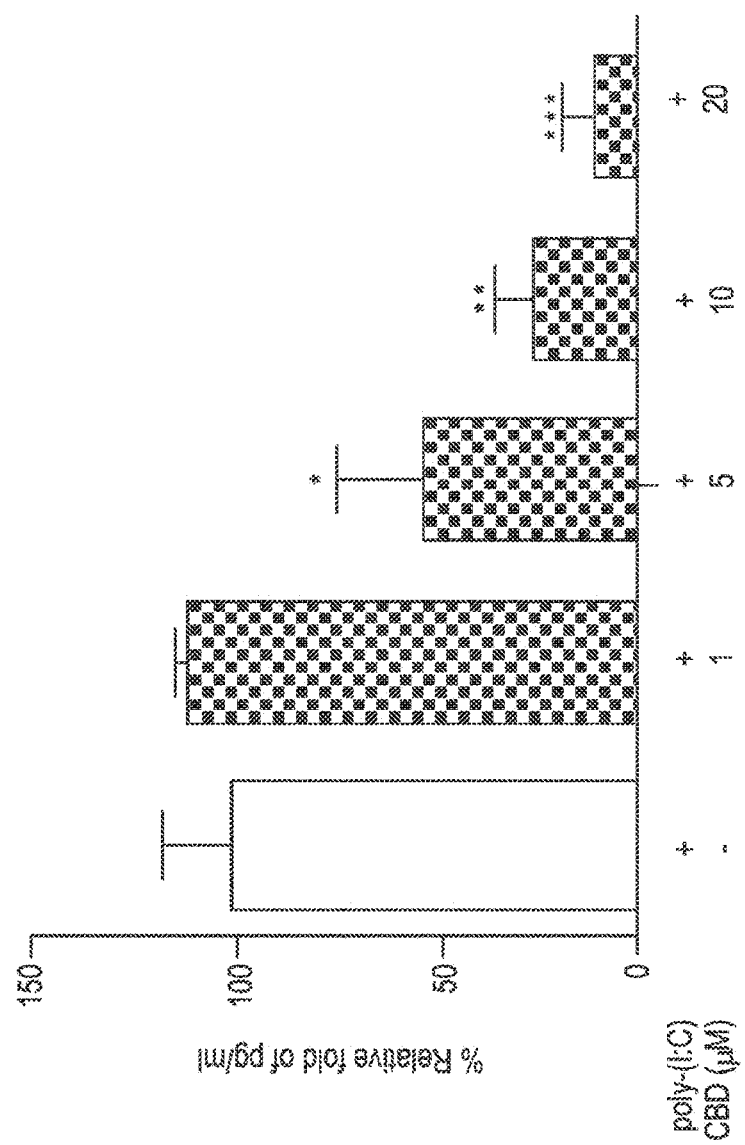
FIG. 9 shows an ELISA assay for MCP-2 release in the supernatants of poly-(I:C)-stimulated HaCaT cells in presence of vehicle or CBD.
Figure 10:
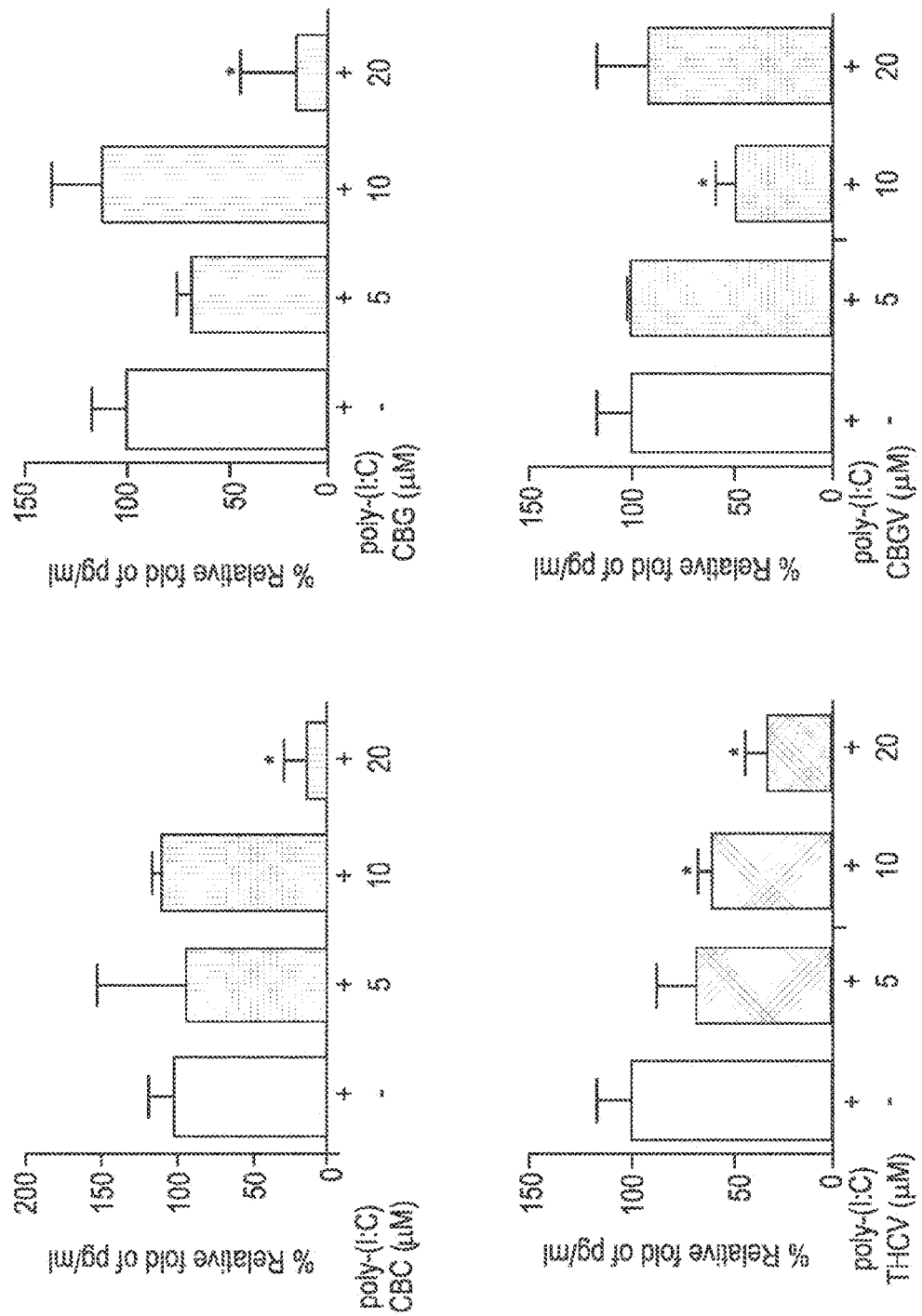
FIG. 10 shows an ELISA assay for MCP-2 release in the supernatants of poly-(I:C)-stimulated HaCaT cells in presence of vehicle or CBC (A), CBG (B), THCV (C) and CBGV (D)

When HaCaT cells were co-stimulated with poly-(I:C) and CBD (1, -5-, 10- and 20 µM), a strong concentration-dependent reduction of MCP-2 protein levels as compared to poly-(I:C)-stimulated HaCaT cells treated with vehicle of CBD was observed (FIG. 9).

The maximum effect was observed at highest concentration tested of CBD (20 µM), as compared to poly-(I:C)-stimulated HaCaT cells treated with vehicle of CBD (FIG. 9).

On the contrary, when HaCaT cells were administered with poly-(I:C) and CBC or CBG no effect was observed at low concentrations (5 and –10 µM), although at the highest concentration tested (20 µM) CBC or CBG were able to reduce MCP-2 production (FIG. 10A, B).

Likewise, when HaCaT cells were co-administered with poly-(I:C), THCV had no effect at the lowest concentration tested (5 µM), but at 10 µM and 20 µM THCV was able to reduce MCP-2 production (FIG. 100).

CBGV was able to reduce MCP-2 production only at 10 µM (FIG. 10D).

No effect was observed on MCP-2 protein levels after treatment of poly-(I:C)-stimulated HaCaT cells with CBDA, CBDV, CBDVA, CBGA and THCVA as compared to poly-(I:C)-stimulated HaCaT cells treated with the respective vehicles (data not shown).

Likewise, no significant variation was observed on MCP-2 protein levels after that HaCaT cells were treated with CBD or the other phytocannabinoids alone (at highest concentration tested, 20 µM), i.e. in the absence of poly-(I:

C), as compared to vehicle-treated HaCaT cells (data not shown), indicating that this concentration of CBD was not cytotoxic.

AEA Levels in Poly-(I:C)-Stimulated HaCaT Cells

The effect of CBD (20 µM) on AEA, 2-AG, PEA and OEA levels in poly-(I:C)-stimulated HaCaT cells was measured.

Figure 11:
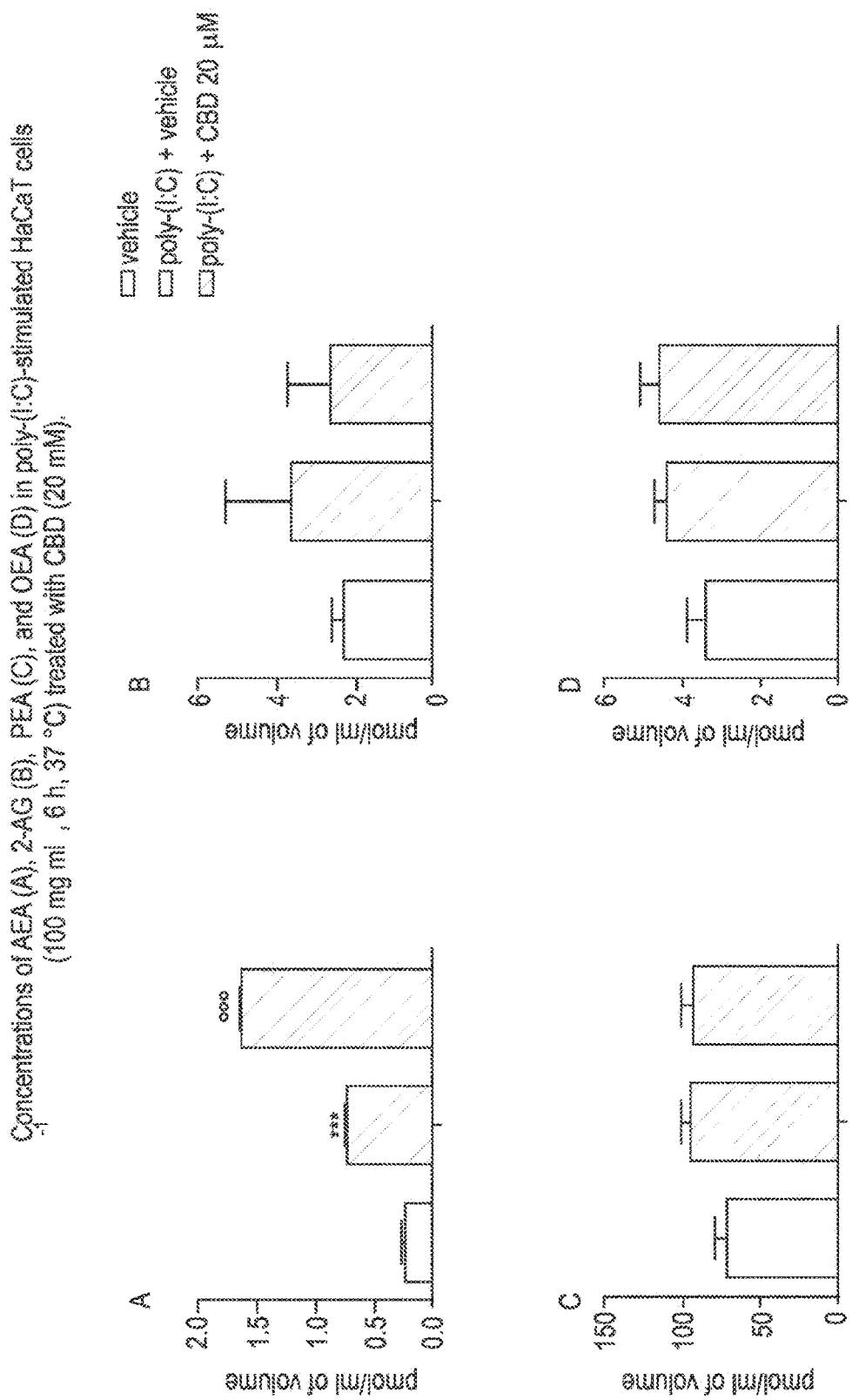
FIG. 11 shows the concentrations of AEA (A), 2-AG (B), PEA (C) and OEA (D) in poly-(I:C)-stimulated HaCaT cells (100 mg·ml-1, 6 h, 37° C.) treated with CBD (20 mM)

It was observed that when HaCaT cells were stimulated with poly-(I:C), AEA levels were significantly increased by ~3-fold compared to vehicle-treated HaCaT cells, and a nearly statistically significant trend towards elevation of PEA levels (P=0.0633) was observed (FIG. 11A,C).

When poly-(I:C)-stimulated HaCaT cells were treated with CBD (20 µM), AEA levels were increased by ~8-fold compared to vehicle-treated HaCaT cells, and by ~2.7-fold compared to poly-(I:C)-stimulated HaCaT cells (FIG. 11A).

No consistent effect of CBD was observed on 2-AG and OEA levels in poly-(I:C)-stimulated HaCaT cells (FIG. 11B, D).

Effect of CBD on Ear Skin Oedema in Mice with DNFB-Induced Allergic Contact Dermatitis (ACD)

The anti-inflammatory effect of CBD in an animal model of ACD was tested. It was observed that only CBD at the highest dose tested (10·mg kg-1, i.p). administered on day 5, 6 and 7 reduced the ear thickness measured 48 and 72 h after the first challenge when compared to control mice (FIG. 12).

Figure 12:
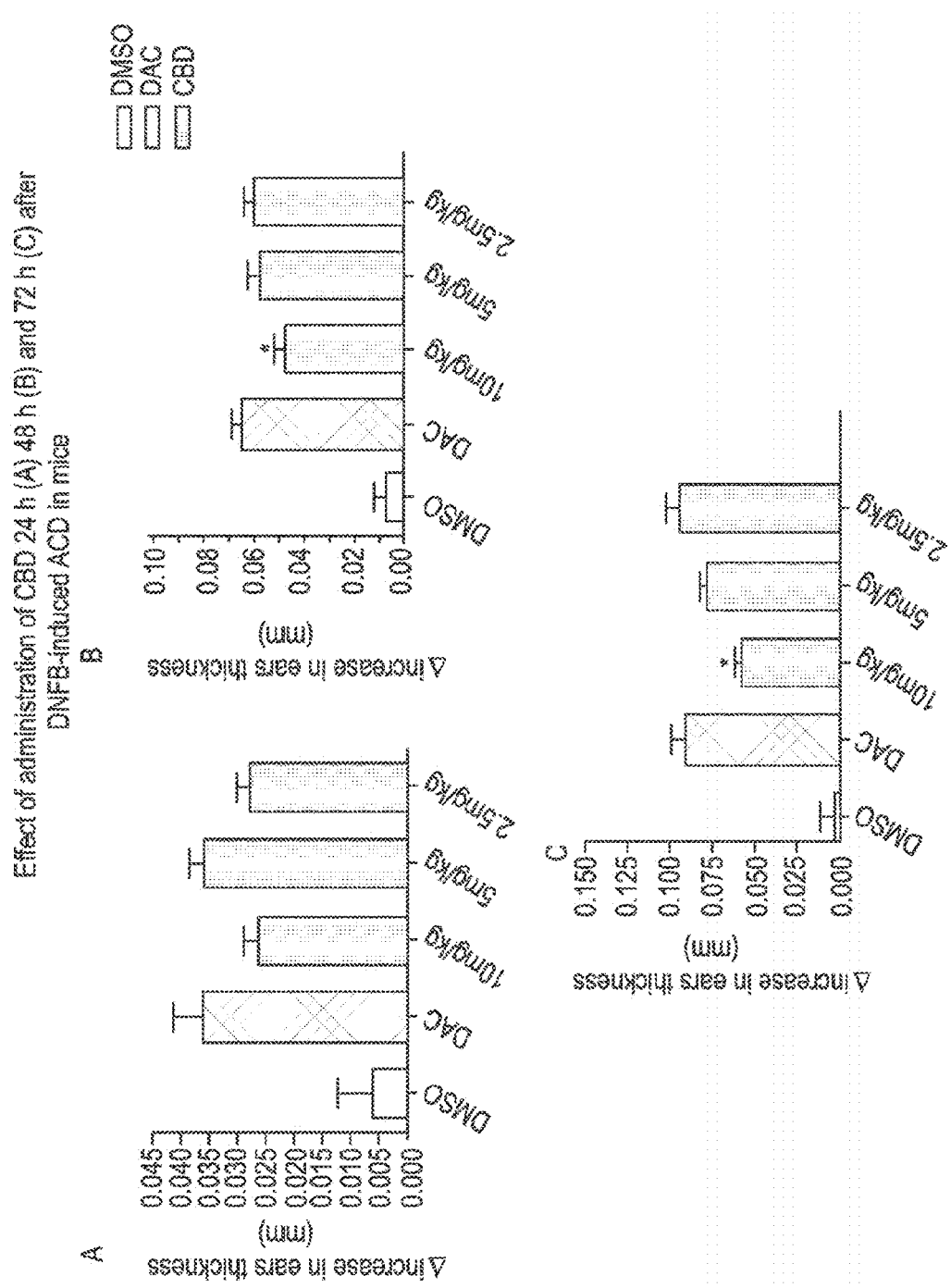
FIG. 12 shows the effect of administration of CBD 24 h (A) 48 h (B) and 72 h (C) after DNFB-induced ACD in mice.

The 2.5 and 5 mg·kg-1 doses did not show any statistically significant effect (FIG. 12).

CONCLUSIONS

CBD was more potent than other phytocannabinoids tested here (CBDA, CBDV, CBDVA, CBC, CBG, CBGA, CBGV, THCV and THCVA), in the inhibition of MCP-2 chemokine production in poly-(I:C)-stimulated keratinocytes cells.

Furthermore, CBD exerts has been shown to produce anti-inflammatory effects in an in vivo model of allergic contact dermatitis (ACD) and as such is a potentially valuable therapeutic treatment option for this disease.

REFERENCES

Sauder, Daniel N. (1990) *The Role of Epidermal Cytokines in Inflammatory Skin Diseases*. Journal of Investigative Dermatology 95, 27S-28S;

Boguslaw Nedoszytko, Malgorzata Sokolowska-Wojdylo, Katarzyna Ruckemann-Dziurdzińska, Jadwiga Roszkiewicz, and Roman J. Nowick. (2014) *Chemokines and cytokines network in the pathogenesis of the inflammatory skin diseases: atopic dermatitis, psoriasis and skin mastocytosis*. Postepy Dermatol Alergol. 2014 May; 31(2): 84-91.

Karsak M, Gaffal E, Date R, Wang-Eckhardt L, Rehnelt J, Petrosino S, et al. (2007). Attenuation of allergic contact dermatitis through the endocannabinoid system. Science 316:1494-1497.

Oláh, A., Tóth, B. I., Borbíró, I., Sugawara, K., Szöllõsi, A. G., Czifra, G., et al. (2014). *Cannabidiol exerts sebostatic and antiinflammatory effects on human sebocytes*. J. Clin. Invest. 124: 3713-3724.

The invention claimed is:

1. A method of treating an inflammatory skin disease comprising administering cannabidiolic acid (CBDA) to a subject in need thereof, wherein the CBDA is administered at a dose of between 10 and 1000 mg, and wherein the inflammatory skin disease is microbial infection-induced dermatitis.

2. The method according to claim 1, wherein the CBDA is in the form of a highly purified extract of cannabis such that it is present at greater than 95% of the total extract (w/w).

3. The method according to claim 1, wherein the CBDA is synthetically produced.

4. The method according to claim 1, wherein the CBDA is used concomitantly with one or more other medicaments.

5. The method according to claim 4, wherein the one or more other medicaments is a corticosteroid.

* * * * *